(12) United States Patent
Almada et al.

(10) Patent No.: US 10,078,135 B1
(45) Date of Patent: Sep. 18, 2018

(54) IDENTIFYING A PHYSICAL DISTANCE USING AUDIO CHANNELS

(71) Applicant: Intel Corporation, Santa Clara, CA (US)

(72) Inventors: Matias Almada, Columbus, GA (US); Xintian Eddie Lin, Palo Alto, CA (US); Songnan Yang, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/497,139

(22) Filed: Apr. 25, 2017

(51) Int. Cl.
| | |
|---|---|
| *H04S 1/00* | (2006.01) |
| *G01S 11/14* | (2006.01) |
| *G10L 19/008* | (2013.01) |
| *G01S 11/16* | (2006.01) |
| *G02B 27/01* | (2006.01) |
| *H04S 3/00* | (2006.01) |
| *H04S 7/00* | (2006.01) |

(52) U.S. Cl.
CPC ............ *G01S 11/14* (2013.01); *G01S 11/16* (2013.01); *G02B 27/017* (2013.01); *G10L 19/008* (2013.01); *H04S 1/007* (2013.01); *H04S 3/008* (2013.01); *H04S 7/30* (2013.01); *A61M 2205/507* (2013.01); *H04S 2400/11* (2013.01)

(58) Field of Classification Search
None
See application file for complete search history.

(56) References Cited

U.S. PATENT DOCUMENTS

| | | | |
|---|---|---|---|
| 8,767,050 B2* | 7/2014 | Bennett | G06F 3/14 348/51 |
| 2017/0208565 A1* | 7/2017 | Lowe | H04W 64/006 |

OTHER PUBLICATIONS

Marziani, Carlos De., et al. (Oct. 2012). Simultaneous Round-Trip Time-of-Flight. IEEE Sensors Journal, 12(10), 2931-2940.
Peng, C., et. al. (Nov. 6-9, 2007). BeepBeep: A High Accuracy Acoustic Ranging System. SenSys'07. Sydney, Australia, 14 pages.

* cited by examiner

*Primary Examiner* — David Bilodeau
(74) *Attorney, Agent, or Firm* — Schwabe, Williamson & Wyatt, P.C.

(57) ABSTRACT

Apparatuses, methods and storage medium associated with identifying a physical distance using audio channels are disclosed herein. In embodiments, an apparatus may include a microphone associated with a first audio channel of a plurality of audio channels and a radio receiver associated with a second different audio channel of the plurality of audio channels. The apparatus may include one or more processors, devices, and/or circuitry to identify an amount of time between times of receipt of first and second representations of a signal received via the microphone over the first audio channel and via the radio receiver over the second audio channel, respectively. The amount of time may be usable to identify a physical distance between references associated with a remote source of the first and second representations and the apparatus, respectively. Other embodiments may be disclosed or claimed.

21 Claims, 5 Drawing Sheets

IDENTIFYING A PHYSICAL DISTANCE USING AUDIO CHANNELS

TECHNICAL FIELD

The present disclosure relates to computing and more specifically relates to identifying a physical distance using audio channels.

BACKGROUND

The background description provided herein is for the purpose of generally presenting the context of the disclosure. Unless otherwise indicated herein, the materials described in this section are not prior art to the claims in this application and are not admitted to be prior art by inclusion in this section.

Mobile computing devices, despite many sophisticated wireless technologies, are missing accurate proximity capabilities. However, accurate proximity capabilities are needed for many applications, such as wireless communications. Some existing proximity capabilities may not achieve millimeter accuracy and/or may require expensive components, however.

Besides the need for accurate proximity capabilities, some applications may also have a need for positioning information. A tracking system for a head mount display (HMD) device for virtual reality (VR) applications may include infrared (IR) receivers mounted on the HMD device, and transmitters mounted around a room may include IR transmitters. The IR transmitters of the mounted transmitters may physically rotate similar to lighthouses in maritime navigation. The IR receivers on the HMD device may read a signal from the rotating IR transmitters to obtain data that can be used to identify a position of the HMD, used for generating VR content.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

Figure 1:
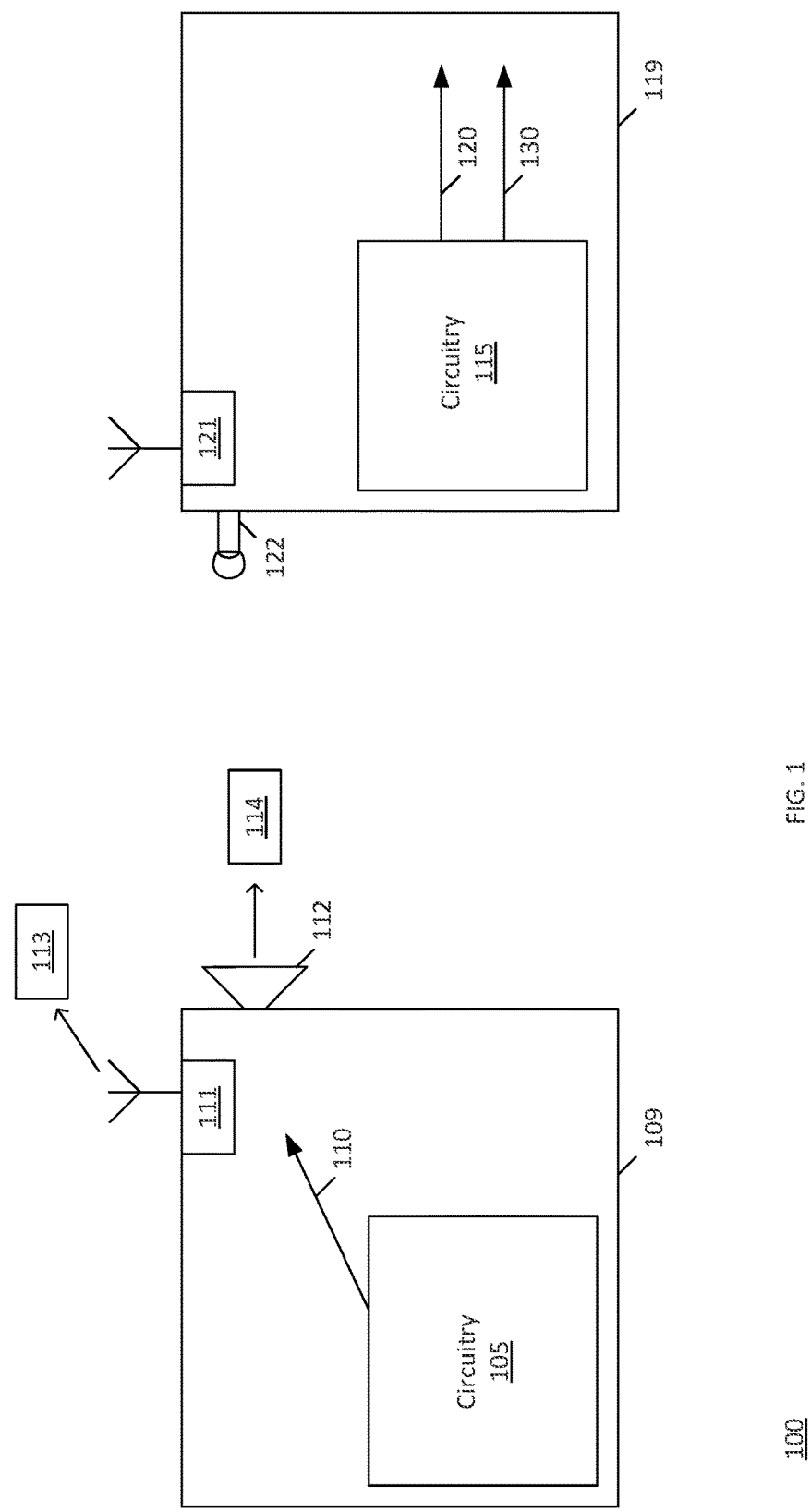
FIG. 1 illustrates an example system equipped with technology for identifying a physical distance using audio channels, according to various embodiments.

Apparatuses, methods and storage medium associated with identifying a physical distance using audio channels are disclosed herein. In embodiments, an apparatus may include a radio receiver associated with a first audio channel of a plurality of audio channels and a microphone associated with a second different audio channel of the plurality of audio channels. The apparatus may include one or more processors, devices, and/or circuitry to identify an amount of time between times of receipt of first and second representations of a signal received via the radio receiver over the first audio channel and via the microphone over the second audio channel, respectively. The amount of time may be usable to identify a physical distance between references associated with a remote source of the first and second representations and the apparatus, respectively.

In the following detailed description, reference is made to the accompanying drawings which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that like elements disclosed below are indicated by like reference numbers in the drawings.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

As used herein, the term "circuitry" may refer to, be part of, or include an Application Specific Integrated Circuit (ASIC), an electronic circuit, a programmable combinational logic circuit (such as a field programmable gate array (FPGA)) a processor (shared, dedicated, or group) and/or memory (shared, dedicated, or group) that execute one or more software or firmware programs, and/or other suitable components that provide the described functionality.

In some embodiments, when mobile devices such as laptops, tablets, phones, or head mount displays within ear shot proximity are to trigger a distance measurement, a first device may transmit an audio pulse through a speaker (e.g., an integrated speaker) while simultaneously transmitting a sync pulse through a radio transmitter. The audio pulse may be in a frequency that is inaudible to human hearing (e.g., above human hearing), and as such may be referred to as an inaudible audio pulse. The audio pulse via the speaker travels non-immediately (e.g., at the speed of sound) to the receiving device where the sound may be recorded via microphone(s), e.g., integrated microphone(s) of a second device. However, the sync pulse may be broadcast via the radio (e.g., at an Industrial, scientific, and medical (ISM) band), and may travel immediately (e.g., at the speed of light) to a radio receiver of the second device.

On the receiver side, a component of the second device (e.g., a codec, an Analog to Digital Convertor (ADC), or the like, or combinations thereof) may record the received signals to identify receipt times of the radio sync pulse and the arriving audio sync pulse. The travel time of the acoustical path from the first device to the second device may be approximately equal to the time difference of the receipt times. This travel time (e.g., this approximation of the travel time) may be used to accurately measure the physical distance between the devices.

The radio transmitter and/or the radio receiver may be integrated on the first device or removably attached to the first device and/or integrated on the second device or removably attached to the second device. In some removable attachment embodiments, the radio transmitter may be an RF (radio frequency) IC (integrated circuit) connected to an audio output of the first device (e.g., a RF-to-Audio dongle inserted into an audio output port, such as a 3.5 mm headphone/earbuds jack in some examples). The radio receiver may be an RF IC connected to an audio input of the second device (e.g., an Audio-to-RF dongle inserted into an audio input port, such as a 3.5 mm microphone jack in some examples).

Some embodiments may utilize devices' legacy audio CODEC (coder-decoder) IC's plural-channel (e.g., multi-channel) playback path and/or plural-channel recording path. Audio signals sent to the transmitter radio may originate from the same interface (e.g., audio codec) as signals outbound to the speaker. Signals intercepted by the receiver radio (e.g., through an audio port) may be sampled by the same interface (e.g., audio codec) corresponding to the microphone. The system may self-synchronize the travel time of the inaudible signal based on a comparison of the recording paths' inputs. The recorded audio traces (e.g., the microphone and radio receiver inputs received by the component such as the codec) may include the time synchronization information. The receiver may not need to keep track of clock error/drift, which may reduce processing calculations (e.g., which may in turn reduce power usage and/or processing requirements) relative to a receiver that is required to keep track of clock error/drift. In some embodiments, accuracy of 0.3 mm to 3 mm (1 to 10 µs) or better may be achieved.

The electric signal (e.g., the radio sync pulse that travels at the speed of light) may be treated by the system as instantaneous. The electric signal may be used as a reference for the time of flight (ToF) of the audio sync pulse. Other systems that identify ToF to perform ranging by ultrasound may not include the electric signal, and may require clock synchronization and/or a reference to a triggering time stamp for calculation of ToF. The components that may be required for clock synchronization and/or a reference to a triggering time stamp may be relatively expensive.

Some legacy systems may utilize ranging with ultrasound based on round trip time measurement. These systems may measure round trip time, and derive one way trip time by calculation based on the round trip time measurement. However, besides the longer travel time, systems utilizing round trip time measurement based on ultrasound may require a device to include both a speaker and a microphone. Furthermore, because the microphone and the speaker cannot exist at the same physical location (each component is located on a different portion of the device), round trip time is not exactly twice one way travel time. This complication may double the parameters involved in deriving one way time based on a round trip time measurement, making it much harder to solve and scale and/or millimeter accuracy may not be achievable. Also, in these systems, every microphone may hear the local speaker signal and remote speaker signals (due to transmit and record at the same time), which may require a relatively high dynamic range in an ADC and therefore limit the range application.

Some embodiments herein utilize a same interface (e.g., a same codec, ADC (on the receiver side), DAC (on the transmitter side), or the like, or combinations thereof). Utilization of a same interface may be different than other possible approaches that may use different interfaces (e.g., radio on a first bus and audio on a second bus, which may require synchronizing bus times for the different buses). Some embodiments utilizing a same interface may process component traces (e.g., codec traces, ADC traces, DAC traces, etc.) to perform a ranging calculation. However, these embodiments may not require time synchronization on multiple interfaces in the same device(s).

In embodiments in which an RF IC is integrated with a plural-channel component (e.g., a plural-channel audio codec, a plural-channel ADC, or the like, or combinations thereof), a reception device may use the transmission of an audio-to-RF and RF-to-audio channel to determine a starting position to find the amount of time until the high frequency inaudible acoustical signal arrives through the microphone input channels of the same plural-channel component. These embodiments may be a cost effect proximity solution for use cases such as device trilateration for Smart Meetings (seating map), indoor Head Mount Display tracking, etc.

In a device tracking scenario, a number of ultrasound transmitters (e.g., three or more) with different ultrasound signatures may be activated. A single microphone may record the ultrasound trace. Together with the radio response, the distances from the microphone to each of the ultrasound transmitters (e.g., speakers) may be estimated. Given the locations of the transmitters, the distances may allow an accurate estimation of the three dimensional location of the microphone through trilateration. Furthermore, with more than one microphone, all 6 degrees of freedom (6DoF) of the object may be established in a virtual reality system utilizing an HMD with more than one microphone.

In embodiments with N transmission device audio channels and M reception device audio channels, one of the audio channels may be replaced with an RF synchronization mechanism. In other words, N-1 transmission device ports may be connected to speakers on the transmitter device and M-1 reception device ports may be connected to microphones on the receiver device. The Nth port on the transmission device may be connected to a broadcast radio and the $M^{th}$ port on the reception device may be connected to a radio receiver. The Nth port of the transmission device may then embed a sync pulse to the $M^{th}$ port of the reception device (which arrives at the speed of light). The other N-1 ports of the transmission device may similarly embed a sync pulse; however, this signal may travel at the speed of sound. The reception device may need only compare the time difference of arrival of the $M^{th}$ sync pulse to the earliest of the M-1 port. The difference in physical displacement between the transmission device and the reception device may be equal to the product of the time difference and a constant (e.g., the speed of sound).

The receiver, depending on orientation and position of microphones, may receive the acoustical signals at varying times. Other time differences can be used to determine physical distances corresponding to the other microphones.

The positioning information may be determined using trilateration based on the physical distances.

FIG. 1 illustrates an example system 100 equipped with technology for identifying a physical distance using audio channels, according to various embodiments. The system 100 may include a transmission device 109 that may include a speaker 112 (e.g., one or more speakers) and a radio transmitter 111, and a reception device 119 that may include a microphone 122 (e.g., one or more microphones) and a radio receiver 121. The transmission device 109 may include circuitry 105 to simultaneously transmit a signal 110 using audio channels associated with the radio transmitter 111 and the speaker 112, respectively. The signal 110 may be include data known to the reception device 119, e.g., predefined data.

The simultaneous transmission may cause representations 113 and 114 of the signal to be received by the reception device 119, through receiver 121 and microphone 122, at different times. The reception device 119 may include circuitry 115 to identify times of receipt 120 and 130 of the representations 113 and 114 of the signal 110, respectively. Any component of the system 100 may identify an amount of time between the times of receipt 120 and 130 and/or calculate a physical distance between a portion of the transmission device 109 and a portion of the reception device 119 based on the amount of time. In some embodiments, the circuitry 115 may perform the identification of the amount of time and/or may calculate of the physical distance based on the amount of time. In other embodiments, the reception device 119 may include an interface (not shown) to send a communication specifying the times of receipt 120 and 130 and/or the amount of time to a remote device, e.g., the transmission device 109 or another device (not shown, of the system 100 or a system coupled to system 100), which may perform the identification and/or calculation. The calculated physical distance may be between the speaker 112 and the microphone 122. This distance can be used to calculate the distance between any other points on the transmission device 109 or the reception device 119 using information about a shape and/or dimensions of the transmission device 109 and/or the reception device 119 and/or a placement of the speaker 112 and/or the microphone 122.

In some embodiments, the transmission device 109 may include one or more additional speakers (not shown) and/or the reception device may include one or more additional microphones (not shown). In embodiments including additional speakers, the circuitry 105 may be to cause one or more additional representations (not shown) similar to representation 114 to be transmitted (each over a different channel and/or via a different speaker). The circuitry 115 may be used to identify one or more additional times of receipt (not shown) similar to time of receipt 130. The one or more additional times of receipt may be used to identify one or more additional amounts of time (e.g., between the time of receipt 120 and each additional representation's time of receipt), which may be used to calculate one or more additional physical distance (e.g., between the microphone 122 and each additional speaker).

In embodiments in which the reception device 119 may include one or more additional microphones, each additional microphone may be associated with a different audio channel. The circuitry 115 may be to identify one or more additional times of receipt (not shown) similar to time of receipt 130. The one or more additional times of receipt may be used to identify one or more additional amounts of time (e.g., between the time of receipt 120 and each additional representation's time of receipt), which may be used to calculate one or more additional physical distances (e.g., between each additional microphone and a reference, such as the speaker 112 or a respective one of speaker 112 and one or more additional speakers).

In embodiments in which additional physical distance(s) may be calculated (because the transmission device 109 include one or more additional speakers and/or the reception device 119 includes one or more additional microphones), the circuitry 105, the circuitry 115 and/or some other device (not shown) may ascertain position information of one of the devices 109 or 119 relative to a reference (e.g., the other of devices 109 or 119) based on trilateration. The position information may be used for localization (e.g., indoor localization) and/or indoor position tracking (e.g., an IPS (indoor positioning system)). The positioning information may include three dimension coordinates (e.g., x, y, x coordinates to identify a position in a space).

Figure 2:
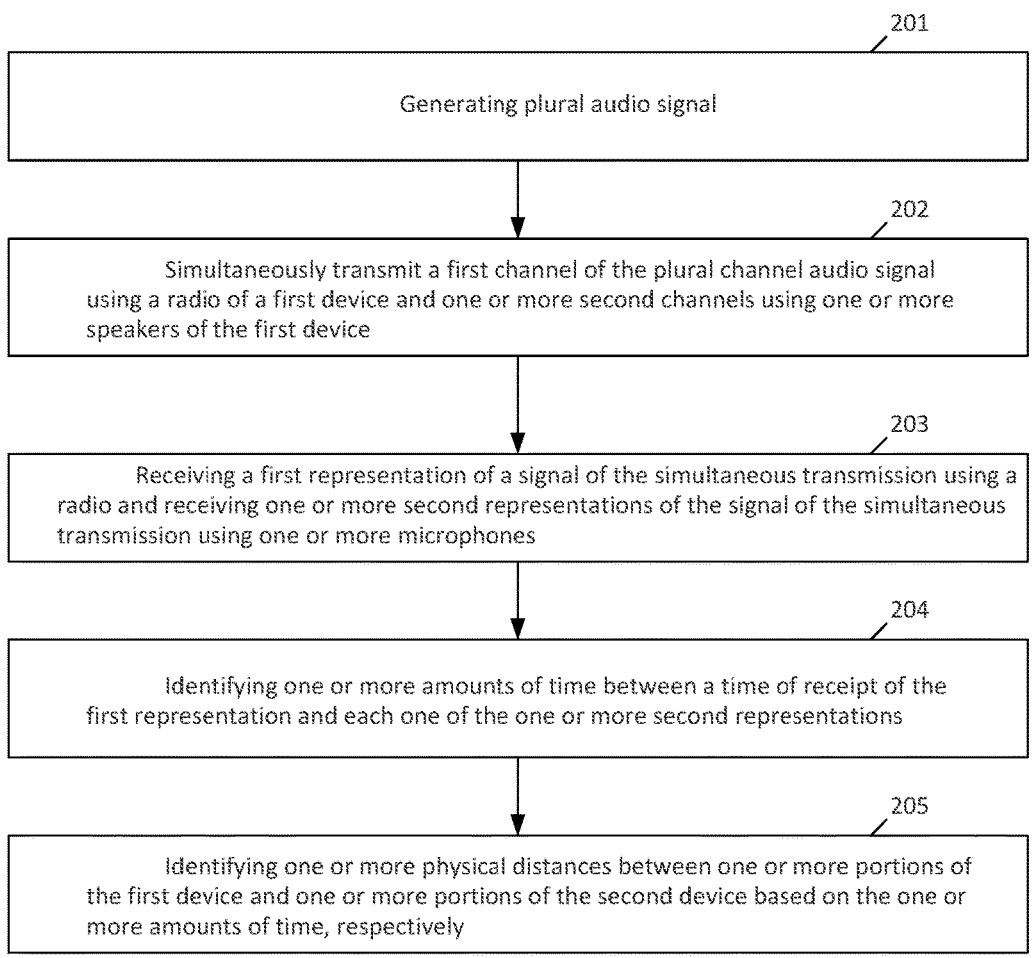
FIG. 2 is a flow chart showing a process of identifying a physical distance using any system described herein.

FIG. 2 is a flow chart showing a process 200 of identifying a physical distance using any system described herein. The system may include a first device similar to transmission device 109 (FIG. 1) and a second device similar to reception device 119 (FIG. 1). In block 201, the system may generate a plural channel audio signal. The plural channel audio signal generated in block 201 may be for at least two channels. In block 202, the system may simultaneously transmit a first channel of the plural channel audio signal using a radio of a first device and one or more second channels using one or more speakers of the first device.

In block 203, the system may receive a first representation of a signal of the simultaneous transmission using a radio of a second device, and may receive one or more second representations of the signal of the simultaneous transmission using one or more microphones of the second device. In block 204, the system may identify one or more amounts of time. Each amount of time may be between a time of receipt of the first representation and a time of receipt of a respective one of the one or more second representations. In block 205, the system may identify one or more physical distances between one or more portions of the first device and one or more portions of the second devices based on the one or more amounts of time, respectively.

Figure 3:
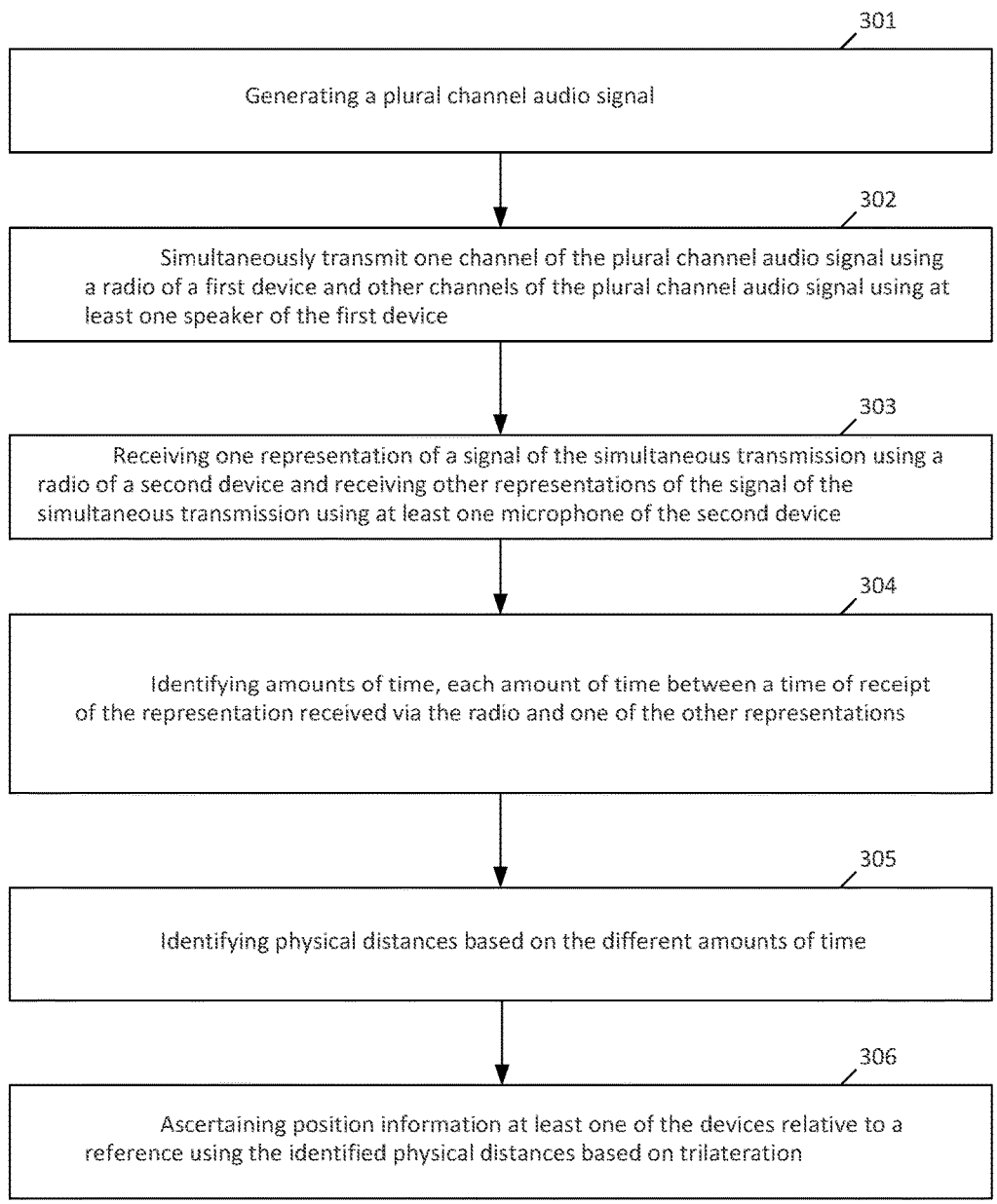
FIG. 3 is a flow chart showing a process of ascertaining position information using any system described herein.

FIG. 3 is a flow chart showing a process 300 of ascertaining position information using any system described herein. The system may include a first device similar to transmission device 109 (FIG. 1) and a second device similar to reception device 119 (FIG. 1).

In block 301, the system may generate a plural audio signal. This plural audio signal may be for three or more audio channels. In block 302, the system may simultaneously transmit a first channel of the plural channel audio signal using a radio of the first device, and simultaneously transmit over other channels using one or more speakers of the first device (in plural speaker examples each speaker may transmit for a respective one of the other channels).

In block 303, the system may receive one representation of a signal of the simultaneous transmission using a radio (of the second device), and may receive other representations of the signal of the simultaneous transmission using one or more microphones of the second device (in plural microphone examples each microphone may receive for a respective one of the other channels).

In block 304, the system may identify amounts of time. Each amount of time may be between a time of receipt of the representation received via the radio and one of the other representation's time of receipt. In block 305, the system may identify physical distances based on the amounts of time.

In block 306, the system may ascertain position information of at least one of the devices relative to a reference point using the identified physical distances based on trilateration. In examples in which the second device is an HMD with microphones on different portions of the surface (e.g., different portions, respectively, of the exterior surface of the HMD), the position information may indicate an orientation of the HMD relative to a reference point (which in turn may indicate whether a user wearing the HMD is looking up, looking down, to the side, etc.) The first device may be a compute device including speakers and a radio. The reference point may be a point on one of the speakers, a midpoint between the speakers, or any other point.

When the HMD is part of a virtual reality system, the positioning information may be used by any component of the virtual reality system to generate a virtual reality display (e.g., images and/or sounds) to be output by display components of the virtual reality system. For example, display components of the virtual reality system may include a display of the HMD (to be viewed while wearing the HMD), speakers integrated into the HMD, and speakers positioned around the room (the speakers positioned around the room may be used to transmit the inaudible acoustic signals).

Figure 4:
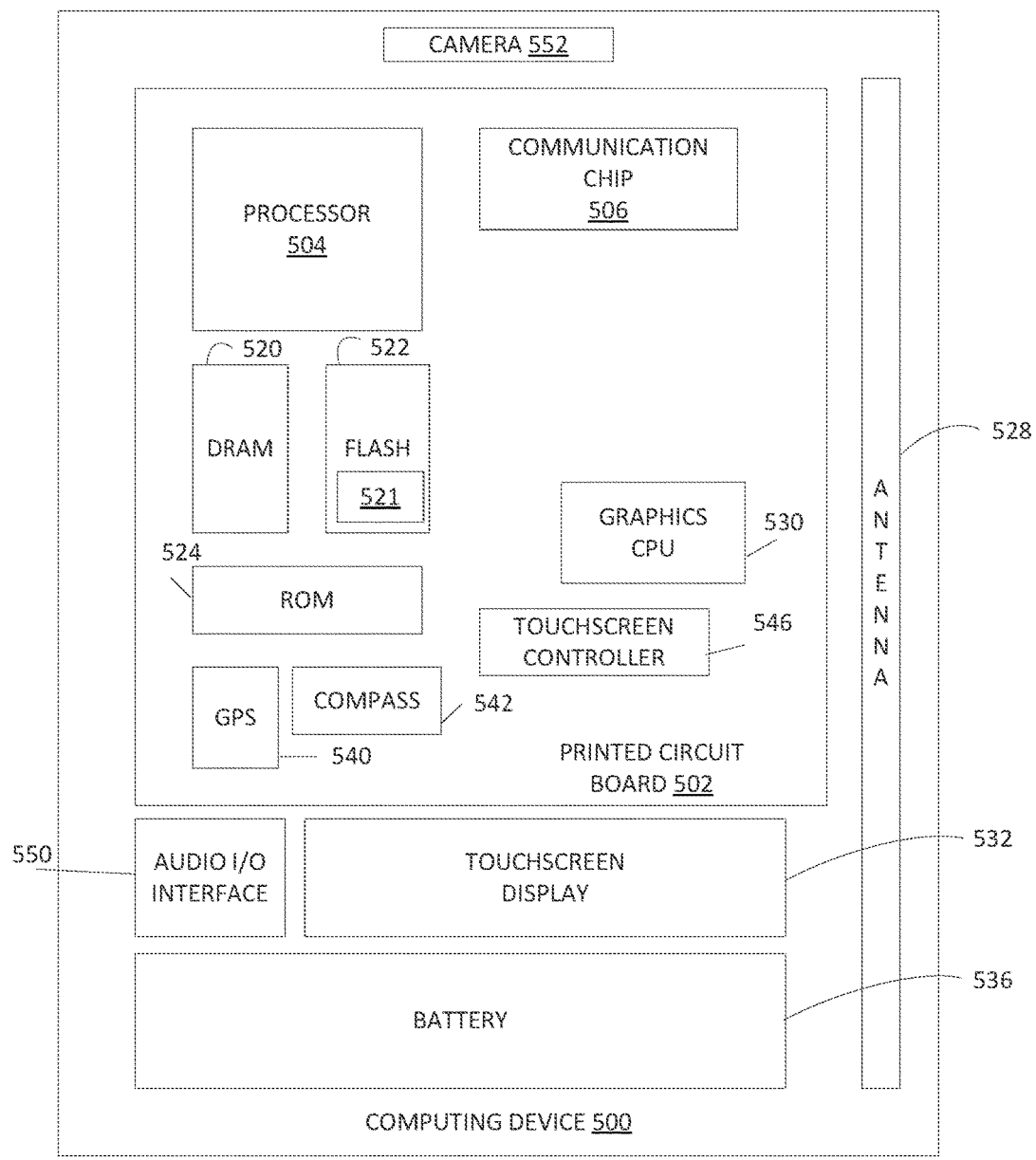
FIG. 4 illustrates an example computing device that may employ the apparatuses and/or methods described herein, according to various embodiments.

FIG. 4 illustrates an example computing device 500 that may employ the apparatuses and/or methods described herein, according to various embodiments (for instance, any apparatus and/or method associated with any compute device or electronic device described earlier with respect to FIGS. 1-3). As shown, device 500 may include a number of components, such as one or more processors 504 (one shown), at least one communication chip 506, and an audio input/output interface 550. The communication chip 506 may have an interface (not shown) to transmit and/or receive an electrical signal (e.g., a radio transmission). The audio input/output interface 550 may include at least one speaker and/or microphone (such as speaker 112 and microphone 122) to transmit or receive an audio pulse.

In various embodiments, the one or more processors 504 each may include one or more processor cores. In various embodiments, the at least one communication chip 506 may be physically and electrically coupled to the one or more processors 504. In further implementations, the communication chip 506 may be part of the one or more processors 504. In various embodiments, computing device 500 may include printed circuit board (PCB) 502. For these embodiments, the one or more processors 504 and communication chip 506 may be disposed thereon.

Depending on its applications, computing device 500 may include other components that may or may not be physically and electrically coupled to the PCB 502. These other components include, but are not limited to, a memory controller (not shown), volatile memory (e.g., dynamic random access memory (DRAM) 520), non-volatile memory such as read only memory (ROM) 524, flash memory 522, an I/O controller (not shown), a digital signal processor (not shown), a crypto processor (not shown), a graphics processor 530, one or more antenna 528, a display (not shown), a touch screen display 532, a touch screen controller 546, a battery 536, an audio codec (not shown), a video codec (not shown), a global positioning system (GPS) device 540, a compass 542, an accelerometer (not shown), a gyroscope (not shown), a camera 552, and a mass storage device (such as hard disk drive, a solid state drive, compact disk (CD), digital versatile disk (DVD)) (not shown), and so forth.

In some embodiments, the one or more processor 504, flash memory 522, and/or a storage device (not shown) may include associated firmware (not shown) storing programming instructions 521 configured to enable computing device 500, in response to execution of the programming instructions by one or more processor 504, to perform methods described herein such as identifying a physical distance using audio channels. In various embodiments, these aspects may additionally or alternatively be implemented using hardware (such as ASIC or FPGA) separate from the one or more processor 504, flash memory 512, or storage device 511.

The communication chips 506 may enable wired and/or wireless communications for the transfer of data to and from the computing device 500. In embodiments, communication chips 506 may include a transmitter and/or receiver similar to transmitter 111 and/or receiver 121 (FIG. 1). The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 506 may implement any of a number of wireless standards or protocols, including but not limited to IEEE 702.20, Long Term Evolution (LTE), LTE Advanced (LTE-A), General Packet Radio Service (GPRS), Evolution Data Optimized (Ev-DO), Evolved High Speed Packet Access (HSPA+), Evolved High Speed Downlink Packet Access (HSDPA+), Evolved High Speed Uplink Packet Access (HSUPA+), Global System for Mobile Communications (GSM), Enhanced Data rates for GSM Evolution (EDGE), Code Division Multiple Access (CDMA), Time Division Multiple Access (TDMA), Digital Enhanced Cordless Telecommunications (DECT), Worldwide Interoperability for Microwave Access (WiMAX), Bluetooth, derivatives thereof, as well as any other wireless protocols that are designated as 3G, 5G, 5G, and beyond. The computing device 500 may include a plurality of communication chips 506. For instance, a first communication chip 506 may be dedicated to shorter range wireless communications such as Wi-Fi and Bluetooth, and a second communication chip 506 may be dedicated to longer range wireless communications such as GPS, EDGE, GPRS, CDMA, WiMAX, LTE, Ev-DO, and others.

In various implementations, the computing device 500 may be a wearable device, a laptop, a netbook, a notebook, an ultrabook, a smartphone, a computing tablet, a personal digital assistant (PDA), an ultra-mobile PC, a mobile phone, a desktop computer, a server, a printer, a scanner, a monitor, a set-top box, an entertainment control unit (e.g., a gaming console or automotive entertainment unit), a digital camera, an appliance, a portable music player, or a digital video recorder. In further implementations, the computing device 500 may be any other electronic device that processes data.

Any combination of one or more computer usable or computer readable medium may be utilized. The computer-usable or computer-readable medium may be, for example but not limited to, an electronic, magnetic, optical, electro-magnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device.

Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Figure 5:
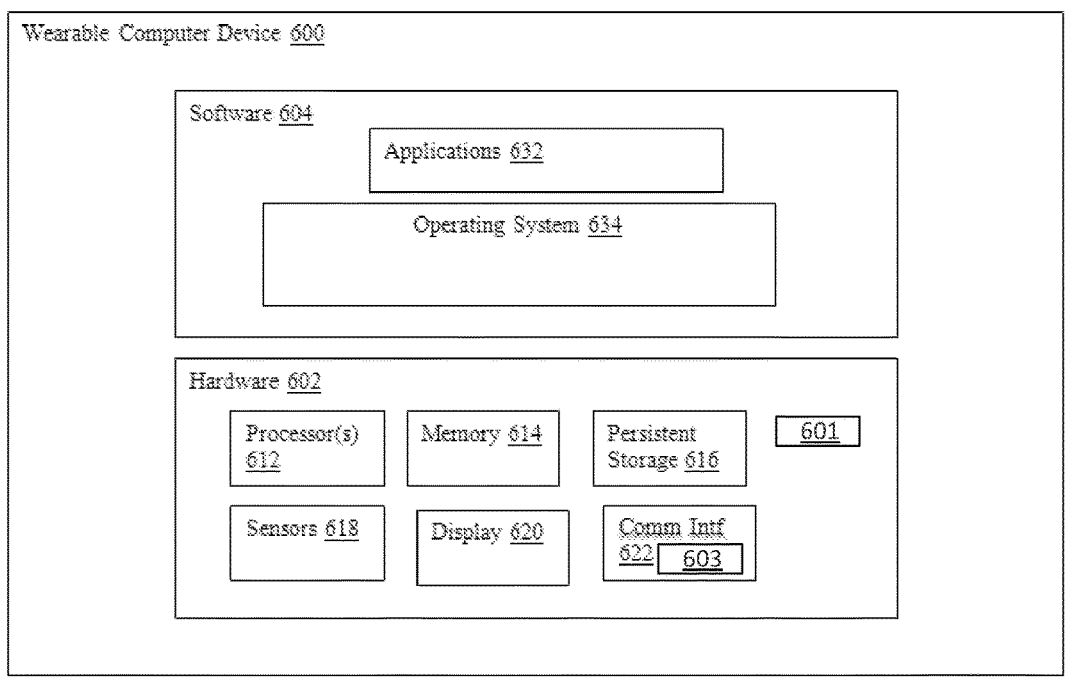
FIG. 5 illustrates example architecture of a wearable computer device, in accordance to various embodiments.

FIG. 5 illustrates example architecture of a wearable computer device 600, in accordance with various embodiments. The wearable computer device 600 may include a communication interface 622 including a radio component 603 (such as a radio receiver) and hardware 602 may include an audio input/put interface 601 (such as one or more microphones).

As illustrated, in embodiments, wearable computer device 600 may include hardware 602 and software 604. Hardware 602 may include one or more components such as processor(s) 612, memory 614, persistent storage 616, sensors 618, the display 620, and the communication interface 622. Communication interface 622 may include any number of wireless communication or networking interfaces known, such as WiFi, 3G/4G, Bluetooth®, Near Field Communication, LiFi, and so forth. In some examples, the radio component 602 may utilize an antenna to support one or more of the wireless communication or networking interfaces of the communication interface 622 (such as an NFC antenna). Display 620 may be any known display device.

Processor(s) 612 may be any one of a number of processors known in the art, each having one or more processor cores. Memory 614 may be any known volatile or non-volatile memory in the art, suitable for storing instructions for execution and working data, in particular, instructions and data of applications 632 and OS 634. Memory 614 may include a hierarchy of cache memory and system memory. Both the cache and system memory may be respectively organized into segments and pages. Persistent storage 616 may be any known persistent mass storage suitable for providing persistent storage of instructions and data of applications 632 and OS 634, e.g., solid state storage, magnetic or optical disk drives. Sensors 618 may include any known sensors of a wearable device. Software 604 may include operating system (OS) 634 and application 632. OS 634 may be any one of a number of wearable computer device OS known in art. Applications 632 may likewise be any one of a number of known applications for wearable computer devices, e.g., virtual reality applications. In embodiments, applications 632 include an application to determine the distance with another device, or to provide audio signals to the other device to determine their distance, as earlier described.

Examples

Example 1 is an apparatus for identifying a physical distance using audio channels. The apparatus may include a microphone associated with a first audio channel of a plurality of audio channels; a radio receiver associated with a second different audio channel of the plurality of audio channels; and circuitry to identify an amount of time between times of receipt of first and second representations of a signal received via the microphone over the first audio channel and via the radio receiver over the second audio channel, respectively, wherein the amount of time is used to identify a physical distance between a reference associated with the apparatus and a reference associated with a remote source of the first and second representations of the signal.

Example 2 includes the subject matter of example 1 (or any other example described herein), wherein the circuitry is to calculate the physical distance between the references based on the amount of time.

Example 3 includes the subject matter of any of examples 1-2 (or any other example described herein), further comprising: one or more additional microphones respectively associated with one or more additional audio channels of the plurality of audio channels; wherein the circuitry is to identify one or more additional amounts of time, each additional amount of time between a time of receipt of the signal received over a respective one of the one or more additional audio channels and the time of receipt of the second representation of the signal over the second audio channel; wherein the circuitry is to calculate one or more physical distances between a different reference associated with the apparatus and the reference associated with the remote source, respectively, based on the one or more additional amounts of time; and wherein the circuitry is to ascertain position information based on the physical distances and trilateration.

Example 4 includes the subject matter of any of examples 1-3 (or any other example described herein), wherein the radio receiver comprises an adapter coupled to an audio input of the apparatus.

Example 5 includes the subject matter of any of examples 1-4 (or any other example described herein), wherein the audio input comprises a microphone jack.

Example 6 includes the subject matter of any of examples 1-5 (or any other example described herein), wherein the circuitry comprises an interface associated with the plurality of audio channels.

Example 7 includes the subject matter of any of examples 1-6 (or any other example described herein), wherein the interface comprises at least one of a plural channel codec or a plural channel Analog to Digital Convertor (ADC).

Example 8 includes the subject matter of any of examples 1-7 (or any other example described herein), wherein the apparatus comprises a wearable device.

Example 9 includes the subject matter of any of examples 1-8 (or any other example described herein), wherein the circuitry is to localize the wearable device, and the localization of the wearable device is used to generate content for the wearable device.

Example 10 includes the subject matter of any of examples 1-9 (or any other example described herein), the wearable device comprises a virtual reality head mount display.

Example 11 is an apparatus for identifying a physical distance using audio channels. The apparatus may include a speaker associated with a first audio channel of a plurality of audio channels; a radio transmitter associated with a second different audio channel of the plurality of audio channels; and circuitry to simultaneously transmit a signal using the first and second audio channels to cause first and second representations of the signal to be output using the speaker and the radio transmitter, respectively, wherein the simultaneous transmission is used to identify a physical distance between references associated with the apparatus and the remote target device, respectively.

Example 12 includes the subject matter of example 11 (or any other example described herein), wherein the radio transmitter comprises an adapter coupled to an audio output of the apparatus.

Example 13 includes the subject matter of any of examples 11-12 (or any other example described herein), wherein the audio output comprises a headphone jack.

Example 14 includes the subject matter of any of examples 11-13 (or any other example described herein), wherein the circuitry is to transmit the signal using one or more additional audio channels that are of the plurality of audio channels and associated with the speaker.

Example 15 includes the subject matter of any of examples 11-14 (or any other example described herein), wherein the signal transmitted using the one or more additional audio channels is used to identify one or more physical distances between the reference associated with the apparatus or one or more different references associated with the apparatus and the reference associated with the remote target device or one or more different references associated with the remote target device, respectively, for ascertainment of a position of the remote target device relative based on trilateration.

Example 16 is a method of identifying a physical distance using audio channels. The method may include performing at least one of simultaneously transmitting a signal using first audio channels associated with a speaker and a radio transmitter, respectively, or receiving first and second representations of the signal over second audio channels via a microphone and radio receiver, respectively; and identifying a physical distance between a reference associated with the speaker and a reference associated with the microphone based on a difference between a time of receipt of the first representation and a time of receipt of the second representation Example 17 includes the subject matter of example 16 (or any other example described herein), further comprising transmitting the signal using one or more additional audio channels that are of the first audio channels and associated with the speaker.

Example 18 includes the subject matter of any of examples 16-17 (or any other example described herein), further comprising identifying one or more different physical distances between the reference associated with the speaker or one or more different references associated with the speaker and the reference associated with the microphone or one or more difference references associated with the microphone based on a difference between a time of receipt of the second representation and a time of receipt one or more additional representations of the signal, respectively.

Example 19 includes the subject matter of any of examples 16-18 (or any other example described herein), further comprising receiving one or more additional representations of the signal over one or more additional audio channels that are of the second audio channels and associated with the microphone.

Example 20 includes the subject matter of any of examples 16-19 (or any other example described herein), further comprising identifying one or more different physical distances between the reference associated with the speaker or one or more different references associated with the speaker and the reference associated with the microphone or one or more different references associated with the microphone based on a difference between a time of receipt of the second representation and a time of receipt of the one or more additional representations of the signal, respectively.

Example 21 is a non-transitory computer-readable medium for determining a physical distance using audio channels. The non-transitory computer-readable medium may include compute device-executable instructions, wherein the instructions, in response to execution by a processor, cause the processor to: identify an amount of time between times of receipt of first and second representations of a signal received via a microphone over a first audio channel of a plurality of audio channels of an interface and via a radio receiver over a second audio channel of the plurality of audio channels, respectively; and determine a physical distance between a reference associated with the microphone and a reference associated with a source of the first representation based on the amount of time.

Example 22 includes the subject matter of example 21 (or any other example herein), wherein the instructions further cause the processor to: identify one or more additional amounts of time between the time of receipt of the second representation and one or more times of receipt of one or more additional representations of the signal received over one or more additional audio channels of the plurality of audio channels; and determine one or more additional physical distances based on the one or more additional amounts of time.

Example 23 includes the subject matter of any of examples 21-22 (or any other example described herein), wherein the instructions further cause the processor to ascertain a position of an electronic device to which the microphone is coupled based on trilateration using the physical distance and the one or more additional physical distances, wherein the position is relative to the reference associated with the source of the first representation.

Example 24 includes the subject matter of any of examples 21-23 (or any other example described herein), wherein the instructions further cause the processor to generate a virtual reality display based on the position.

Example 25 includes the subject matter of any of examples 21-24 (or any other example described herein), further comprising transmitting a communication that includes information about the physical distance to remote device.

Example 26 is an apparatus for identifying a physical distance using audio channels. The apparatus may include means for transmitting an ultrasound representation of a signal using a first audio channel of an interface; means for transmitting a radio frequency (RF) representation using a second audio channel of the interface and at a same time as a transmission of the ultrasound representation of the signal using the first audio channel; and means for identifying a physical distance of a remote electronic device from a reference based on a difference of a time of receipt of the ultrasound representation by the remote electronic device and a time of receipt of the RF representation by the remote electronic device.

Example 27 includes the subject matter of example 26 (or any other example herein), further comprising means for identifying an orientation of the remote electronic device relative to the reference based on the physical distance.

Example 28 includes the subject matter of any of examples 26-27 (or any other example herein), further comprising means for generating content for the remote electronic device based on the orientation.

Example 29 includes the subject matter of any of examples 26-28 (or any other example herein), wherein the content comprises an image of a virtual reality display.

Example 30 includes the subject matter of any of examples 26-29 (or any other example herein), wherein the content comprises a sound of a virtual reality display.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second or third) for identified elements are used to distinguish between the elements, and do not indicate or imply a required or limited number of such elements, nor do they indicate a particular position or order of such elements unless otherwise specifically stated.

What is claimed is:

1. An apparatus, comprising:
a plural channel codec or plural channel Analog to Digital Convertor (ADC);
a microphone to input to a first audio channel of a plurality of audio channels associated with the plural channel codec or plural channel ADC;
first conversion circuitry to input to a second audio channel of the plurality of audio channels, the first conversion circuitry to convert RF (radio frequency) to audio;
a radio receiver to input to the first conversion circuitry;
second circuitry to identify an amount of time between times of receipt of a first value recovered from an audio pulse captured by the microphone and a second value recovered from a radio pulse captured by the radio receiver, respectively; and
a bus extending from the plural channel codec or the plural channel ADC to the second circuitry;
wherein the second circuitry is further to receive first and second data from the plural channel codec or plural channel ADC over the bus, the first and second data derived from the audio pulse and the radio pulse, respectively, and including the first and second values, respectively; and
wherein the amount of time is used by the second circuitry or a remote device to identify a physical distance between a reference associated with the apparatus and a reference associated with a remote source of the audio pulse and the radio pulse.

2. The apparatus of claim 1, wherein the second circuitry is to calculate the physical distance between the references based on the amount of time.

3. The apparatus of claim 2, further comprising:
one or more additional microphones to input to one or more additional audio channels of the plurality of audio channels, respectively;
wherein the second circuitry is to identify one or more additional amounts of time responsive to receiving third data over the bus, the third data derived from one or more additional audio pulses captured by the one or more additional microphones, respectively, each additional amount of time between a time of receipt of the second value and a respective one of one or more third values of the third data, the one or more third values recovered from the one or more additional audio pulses, respectively;
wherein the second circuitry is to calculate one or more physical distances between a different reference associated with the apparatus and the reference associated with the remote source, respectively, based on the one or more additional amounts of time; and
wherein the circuitry is to ascertain position information based on the physical distances and trilateration.

4. The apparatus of claim 1, wherein the radio receiver comprises an adapter coupled to an audio input of the apparatus.

5. The apparatus of claim 4, wherein the audio input comprises a microphone jack.

6. The apparatus of claim 1, wherein the apparatus comprises a wearable device.

7. The apparatus of claim 6, wherein the circuitry is to localize the wearable device, and the localization of the wearable device is used to generate content for the wearable device.

8. The apparatus of claim 6, wherein the wearable device comprises a virtual reality head mount display.

9. An apparatus, comprising:
a plural channel codec or plural channel Digital to Analog Convertor (DAC);
a speaker coupled to a first audio channel of a plurality of audio channels associated with an output of the plural channel codec or plural channel DAC;
first conversion circuitry coupled to a second audio channel of the plurality of audio channels, the first conversion circuitry to convert audio to RF (radio frequency);
a radio transmitter coupled to an output of the first conversion circuitry; and
second circuitry to simultaneously transmit an audio pulse using the speaker based on first data corresponding to the first audio channel and a radio pulse using the radio transmitter based on second data corresponding to the second audio channel of the first conversion circuitry, wherein the simultaneous transmission of the audio pulse and the radio pulse is arranged for identification of a physical distance between references associated with the apparatus and a remote target device, respectively.

10. The apparatus of claim 9, wherein the radio transmitter comprises an adapter coupled to an audio output of the apparatus.

11. The apparatus of claim 10, wherein the audio output comprises a headphone jack.

12. The apparatus of claim 9, wherein the second circuitry is to transmit one or more additional audio pulses based on third data corresponding to one or more additional audio channels of the plurality of audio channels.

13. The apparatus of claim 12, wherein the transmission of the one or more additional audio pulses is simultaneous with the transmission of the radio pulse and arranged for identification of one or more physical distances between the reference associated with the apparatus or one or more different references associated with the apparatus and the reference associated with the remote target device or one or more different references associated with the remote target device, respectively, for ascertainment of a position of the remote target device relative to the apparatus based on trilateration.

14. A method, comprising:
simultaneously transmitting an audio pulse using a speaker coupled to a first audio channel of a plurality of audio channels and a radio pulse using a radio transmitter coupled to an audio-to-RF (radio frequency) convertor coupled to a second audio channel of the plurality of audio channels; and
identifying a physical distance between a reference associated with the speaker and a reference associated with a microphone to capture the audio pulse based on a difference between a time of receipt of a first value recovered from the audio pulse and a time of receipt of a second value recovered from the radio pulse.

15. The method of claim 14, further comprising transmitting one or more additional audio pulses corresponding to one or more additional audio channels of the plurality of audio channels.

16. The method of claim 15, further comprising identifying one or more different physical distances between the reference associated with the speaker or one or more different references associated with the speaker and the reference associated with the microphone or one or more different references associated with the microphone based on a difference between a time of receipt of the second value and a time of receipt of one or more third values recovered from the one or more additional audio pulses, respectively.

17. A non-transitory computer-readable medium comprising compute device-executable instructions, wherein the instructions, in response to execution by a processor, cause the processor to:
identify an amount of time between times of receipt of a first value and a second value, the first value recovered from an audio pulse received via a microphone coupled to a first audio channel of a recording path that includes a plural channel codec or plural channel Analog-to-Digital Convertor (ADC), the second value recovered from a radio pulse received via a radio receiver coupled to an RF-to-audio convertor coupled to a second audio channel of the recording path; and
determine a physical distance between a reference associated with the microphone and a reference associated with a source of the audio pulse based on the amount of time.

18. The non-transitory computer-readable medium of claim 17, wherein the instructions further cause the processor to:
identify one or more additional amounts of time between the time of receipt of the second value and one or more times of receipt of one or more third values of one or more additional audio pulses, respectively; and
determine one or more additional physical distances based on the one or more additional amounts of time, respectively.

19. The non-transitory computer-readable medium of claim 18, wherein the instructions further cause the processor to ascertain a position of an electronic device to which the microphone is coupled based on trilateration using the physical distance and the one or more additional physical distances, wherein the position is relative to the reference associated with the source of the audio pulse.

20. The non-transitory computer-readable medium of claim 19, wherein the instructions further cause the processor to generate a virtual reality display based on the position.

21. The non-transitory computer-readable medium of claim 17, further comprising transmitting a communication that includes information about the physical distance to a remote device.

* * * * *